United States Patent
Rabinovitz et al.

(10) Patent No.: US 8,663,093 B2
(45) Date of Patent: Mar. 4, 2014

(54) DEVICE, SYSTEM AND METHOD FOR IN-VIVO ANALYSIS

(75) Inventors: Elisha Rabinovitz, Haifa (IL); Emil-Israel Katz, Savyon (IL)

(73) Assignee: Given Imaging Ltd., Yoqneam (IL)

(*) Notice: Subject to any disclaimer, the term of this patent is extended or adjusted under 35 U.S.C. 154(b) by 841 days.

(21) Appl. No.: 12/294,656

(22) PCT Filed: Apr. 10, 2007

(86) PCT No.: PCT/IL2007/000458
§ 371 (c)(1), (2), (4) Date: Jul. 8, 2009

(87) PCT Pub. No.: WO2007/113839
PCT Pub. Date: Oct. 11, 2007

(65) Prior Publication Data
US 2009/0318766 A1 Dec. 24, 2009

Related U.S. Application Data

(60) Provisional application No. 60/788,114, filed on Apr. 3, 2006.

(51) Int. Cl.
 *A61B 1/00* (2006.01)
 *A61B 1/04* (2006.01)
 *A61B 1/06* (2006.01)
 *A61B 5/00* (2006.01)
(52) U.S. Cl.
 USPC ........... 600/117; 600/103; 600/118; 600/160; 600/178; 600/300
(58) Field of Classification Search
 USPC .......... 600/103, 117, 118, 160, 178, 300, 317
 See application file for complete search history.

(56) References Cited

U.S. PATENT DOCUMENTS

| 3,971,362 A | 7/1976 | Pope et al. |
| 4,017,261 A | 4/1977 | Svoboda et al. |
| 4,038,485 A | 7/1977 | Johnston et al. |
| 4,239,040 A | 12/1980 | Hosoya et al. |
| 4,278,077 A | 7/1981 | Mizumoto |

(Continued)

FOREIGN PATENT DOCUMENTS

| CA | 2330937 | 12/1999 |
| DE | 3440177 | 5/1986 |

(Continued)

OTHER PUBLICATIONS

International Search Report for International Application No. PCT/IL07/00458, mailed Mar. 18, 2008.

(Continued)

*Primary Examiner* — Philip R Smith
*Assistant Examiner* — Rynae Boler
(74) *Attorney, Agent, or Firm* — Pearl Cohen Zedek Latzer Baratz LLP

(57) ABSTRACT

An in-vivo imaging device, typically an autonomous capsule, having a housing, the housing comprising a window; an illumination source located within the housing to illuminate a body lumen through the window; an imager to receive light reflected from the body lumen through the window; and a transmitter to transmit image data to a receiving system. The window is coated with liposomes containing a marker such that the imager may acquire images which include the marking.

8 Claims, 5 Drawing Sheets

(56) References Cited

U.S. PATENT DOCUMENTS

| | | | |
|---|---|---|---|
| 4,337,222 A | 6/1982 | Kitajima et al. | |
| 4,439,197 A | 3/1984 | Honda et al. | |
| 4,605,630 A * | 8/1986 | Kung et al. | 435/5 |
| 4,689,621 A | 8/1987 | Kleinberg | |
| 4,803,992 A | 2/1989 | Lemelson | |
| 4,844,076 A | 7/1989 | Lesho et al. | |
| 4,885,077 A | 12/1989 | Karakelle et al. | |
| 4,920,045 A | 4/1990 | Okuda et al. | |
| 5,042,486 A | 8/1991 | Pfeiler et al. | |
| 5,081,040 A | 1/1992 | Patel et al. | |
| 5,109,870 A | 5/1992 | Silny et al. | |
| 5,114,864 A | 5/1992 | Walt | |
| 5,173,406 A | 12/1992 | Hosoda | |
| 5,211,165 A | 5/1993 | Dumoulin et al. | |
| 5,252,494 A | 10/1993 | Walt | |
| 5,279,607 A | 1/1994 | Schentag et al. | |
| 5,306,623 A | 4/1994 | Kiser et al. | |
| 5,330,427 A | 7/1994 | Weissenburger | |
| 5,362,478 A | 11/1994 | Desai et al. | |
| 5,385,846 A | 1/1995 | Kuhn et al. | |
| 5,395,366 A | 3/1995 | D—Andrea et al. | |
| 5,429,132 A | 7/1995 | Guy et al. | |
| 5,443,701 A | 8/1995 | Willner et al. | |
| 5,447,868 A | 9/1995 | Augurt | |
| 5,460,969 A | 10/1995 | Fielder et al. | |
| 5,479,935 A | 1/1996 | Essen-Moller | |
| 5,490,969 A | 2/1996 | Bewlay et al. | |
| 5,558,640 A | 9/1996 | Pfeiler et al. | |
| 5,563,071 A | 10/1996 | Augurt | |
| 5,604,531 A | 2/1997 | Iddan et al. | |
| 5,762,770 A | 6/1998 | Pritchard et al. | |
| 5,800,350 A | 9/1998 | Coppleson et al. | |
| 5,814,525 A | 9/1998 | Renschler et al. | |
| 5,819,736 A | 10/1998 | Avny et al. | |
| 5,833,602 A | 11/1998 | Osemwota | |
| 5,833,603 A | 11/1998 | Kovacs et al. | |
| 5,837,196 A | 11/1998 | Pinkel et al. | |
| 5,853,005 A | 12/1998 | Scanlon | |
| 5,892,144 A | 4/1999 | Meller et al. | |
| 5,913,820 A | 6/1999 | Bladen et al. | |
| 5,916,176 A | 6/1999 | Caillouette | |
| 5,919,633 A * | 7/1999 | Tausk et al. | 435/7.1 |
| 5,932,480 A | 8/1999 | Maruo et al. | |
| 5,968,765 A | 10/1999 | Grage et al. | |
| 5,993,378 A | 11/1999 | Lemelson | |
| 6,043,080 A | 3/2000 | Lipshutz et al. | |
| 6,080,423 A | 6/2000 | Charych et al. | |
| 6,099,482 A | 8/2000 | Brune et al. | |
| 6,149,581 A | 11/2000 | Klingenstein | |
| 6,162,469 A | 12/2000 | Atarashi | |
| 6,240,312 B1 | 5/2001 | Alfano et al. | |
| 6,285,897 B1 | 9/2001 | Kilcoyne et al. | |
| 6,330,464 B1 | 12/2001 | Colvin, Jr. et al. | |
| 6,369,812 B1 | 4/2002 | Iyriboz et al. | |
| 6,395,562 B1 | 5/2002 | Hammock et al. | |
| 6,453,928 B1 | 9/2002 | Kaplan et al. | |
| 6,475,145 B1 | 11/2002 | Baylor | |
| 6,488,694 B1 | 12/2002 | Lau et al. | |
| 6,766,817 B2 | 7/2004 | Da Silva | |
| 6,918,404 B2 | 7/2005 | Da Silva | |
| 7,066,586 B2 | 6/2006 | Da Silva | |
| 7,684,840 B2 * | 3/2010 | Palti | 600/310 |
| 2001/0035902 A1 | 11/2001 | Iddan et al. | |
| 2002/0001695 A1 | 1/2002 | Tajima et al. | |
| 2002/0015952 A1 | 2/2002 | Anderson et al. | |
| 2002/0042562 A1* | 4/2002 | Meron et al. | 600/361 |
| 2002/0103417 A1 | 8/2002 | Gazdzinski | |
| 2002/0109774 A1 | 8/2002 | Meron et al. | |
| 2002/0111544 A1* | 8/2002 | Iddan | 600/310 |
| 2002/0146368 A1 | 10/2002 | Meron et al. | |
| 2002/0173718 A1 | 11/2002 | Frisch et al. | |
| 2002/0177779 A1 | 11/2002 | Adler et al. | |
| 2002/0198439 A1 | 12/2002 | Mizuno | |
| 2003/0020810 A1 | 1/2003 | Takizawa et al. | |
| 2003/0023150 A1 | 1/2003 | Yokoi et al. | |
| 2004/0115877 A1 | 6/2004 | Iddan | |
| 2004/0126421 A1 | 7/2004 | Turk et al. | |
| 2005/0075555 A1 | 4/2005 | Glukhovsky et al. | |
| 2005/0131287 A1* | 6/2005 | Kaylor et al. | 600/362 |
| 2008/0114225 A1* | 5/2008 | Rabinovitz | 600/310 |
| 2008/0146896 A1 | 6/2008 | Rabinowitz | |
| 2009/0318766 A1 | 12/2009 | Rabinovitz et al. | |
| 2010/0322866 A1 | 12/2010 | Rabinovitz et al. | |

FOREIGN PATENT DOCUMENTS

| | | |
|---|---|---|
| EP | 1 002 229 | 1/2004 |
| FR | 2 688 997 | 10/1993 |
| JP | 52094681 | 8/1977 |
| JP | 57163309 | 10/1982 |
| JP | 61 502700 | 11/1986 |
| JP | 62240038 | 10/1987 |
| JP | 63 309864 | 12/1988 |
| JP | 4109927 | 4/1992 |
| JP | 4138128 | 5/1992 |
| JP | 4 - 208858 | 7/1992 |
| JP | 5015515 | 1/1993 |
| JP | 5200015 | 8/1993 |
| JP | 5 - 281232 | 10/1993 |
| JP | 5 281233 | 10/1993 |
| JP | 6285044 | 10/1994 |
| JP | 7111985 | 5/1995 |
| JP | 7-191033 | 7/1995 |
| JP | 11 - 500223 | 1/1999 |
| JP | 11509094 | 8/1999 |
| JP | 2001-522353 | 11/2001 |
| JP | 2002-010990 | 12/2001 |
| JP | 2003-513225 | 4/2003 |
| JP | 2004-500006 | 1/2004 |
| JP | 2004-523254 | 8/2004 |
| JP | 2004523274 | 8/2004 |
| JP | 2004529733 | 9/2004 |
| JP | 2004350512 | 12/2004 |
| RU | 2191569 | 10/2002 |
| WO | WO 86/00142 | 1/1986 |
| WO | WO 88/08982 | 11/1988 |
| WO | WO 96/23524 | 8/1996 |
| WO | WO 1997/02357 | 1/1997 |
| WO | WO 97/45720 | 12/1997 |
| WO | WO 98/07366 | 2/1998 |
| WO | WO 99/11754 | 3/1999 |
| WO | WO 99/32028 | 7/1999 |
| WO | WO 00/22975 | 4/2000 |
| WO | WO 01/08548 | 2/2001 |
| WO | WO 2001/053792 | 7/2001 |
| WO | WO 2002/055984 | 7/2002 |
| WO | WO 2002/102243 | 12/2002 |
| WO | WO 2004/014227 | 2/2004 |
| WO | WO 2004/103351 | 12/2004 |
| WO | WO 2004/105946 | 12/2004 |
| WO | WO 2005/003723 | 1/2005 |
| WO | WO 2005/084534 | 9/2005 |
| WO | WO 2005/113374 | 12/2005 |

OTHER PUBLICATIONS

International Search Report for International Application No. PCT/IL07/00457, mailed Aug. 8, 2008.
Supplementary European Search Report for European Application No. 07 73 6198 mailed Mar. 1, 2010.
Supplementary European Search Report, issued Dec. 23, 2009, for European Patent Application No. 06701723.6-2319.
Office Action, issued Jun. 21, 2001, in Japanese Patent Application No. 2007-552809.
Office Action for U.S. Appl. No. 12/294,679 dated Mar. 6, 2012.
Office Action for U.S. Appl. No. 12/294,679 dated Nov. 17, 2011.
Office Action for U.S. Appl. No. 11/831,857 dated Apr. 17, 2012.
Office Action for U.S. Appl. No. 11/883,351 dated Dec. 9, 2011.
Final Office Action for U.S. Appl. No. 10/036,490 dated May 12, 2005.
Office Action for U.S. Appl. No. 09/487,337 dated Mar. 19, 2001.
Office Action for U.S. Appl. No. 09/487,337 dated Jul. 5, 2001.

(56) References Cited

OTHER PUBLICATIONS

Office Action for U.S. Appl. No. 12/294,679 dated Jun. 27, 2012.
Final Office Action for U.S. Appl. No. 12/294,679 dated Oct. 11, 2012.
Video Camera to "TAKE" — RF System Lab, Dec. 25, 2001.
Turke, "New Smart Plastic has Good Memory", European Medical Device Manufacturer, devicelink.com, Sep. 2001.
Rowlands et al., "The Radio Pill", British Communications and Electronics, Aug. 1960, pp. 598-601.
Crum, Wellesley company sends body monitors into space, Apr., 1998.
Swain et al., "Wireless transmission of a color television moving image from the stomach using a miniature CCD camera, light source and microwave transmitter."Gastrointest Endosc, 1197; 45: AB40.
Bruil, "In vitro leucocyte adhesion to modified polyurethane surfaces"; Biomaterials 1992, vol. 13, No. 13.
Medical Diagnosis Reagents, vol. 16.
Lange et al., "Heidelberger Kapsel — ein Kleinstsender fur die pH-Messung im Magen", Telefunken — Zeitung, Jg (1963) Heft 5, pp. 265-270.
Office Action for Japanese Patent Application No. 2007-552809 dated Jan. 24, 2012.
International Search Report for International Application No. PCT/IL2006/00127 dated Dec. 4, 2006.

* cited by examiner

DEVICE, SYSTEM AND METHOD FOR IN-VIVO ANALYSIS

CROSS-REFERENCE TO RELATED APPLICATIONS

This application is a National Phase Application of PCT International Application No. PCT/IL2007/000458, International Filing Date Apr. 10, 2007, which claimed priority from U.S. Provisional Patent Application No. 60/788,114, filed Apr. 3, 2006, which is hereby incorporated by reference.

FIELD OF THE INVENTION

The present invention relates in general to in-vivo analysis, and specifically to in-vivo analysis utilizing liposomes and/or nano-containers.

BACKGROUND OF THE INVENTION

An atypical concentration or presence of substances in body fluids or in body lumens may be indicative of the biological condition of the body. For example, the presence of elevated concentrations of red blood cells in the gastrointestinal (GI) tract may indicate different pathologies, depending on the location of the bleeding along the GI tract. Likewise, abnormalities in physical conditions of the body, such as, for example, elevated temperature, may indicate pathology. Early detection, identification and location of abnormal conditions may be critical for correctly diagnosing and treating various pathologies. Some diseases, for example, cancer, may be detected by analyzing the blood stream for tumor specific markers, e.g., specific antibodies.

Devices and systems for in-vivo imaging may be used, for example, to acquire in-vivo images of the GI tract.

SUMMARY OF THE INVENTION

Some embodiments of the invention may allow, for example, in-vivo analysis. In some embodiments, for example, an in-vivo imaging device may be coated with liposomes or nano-containers containing a marker, an indicator, a signaling agent or a signaling material. The liposomes or nano-containers may react to a certain antigen in-vivo; following the reaction of the liposomes or nano-containers with the antigen, the signaling material may become visible, may become detectable, and/or may modify its optical property. The in-vivo imaging device may acquire images including the signaling material, thereby indicating the in-vivo presence of the antigen that reacts with the liposomes or nano-containers used. In some embodiments, for example, the in-vivo imaging device may be autonomous. In some embodiments, for example, the in-vivo imaging device may include a swallowable capsule.

In some embodiments, for example, a system may include the in-vivo device, which may include a transmitter to transmit the image data to an external receiver and monitor. Embodiments of the invention may provide additional and/or other benefits and/or advantages.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
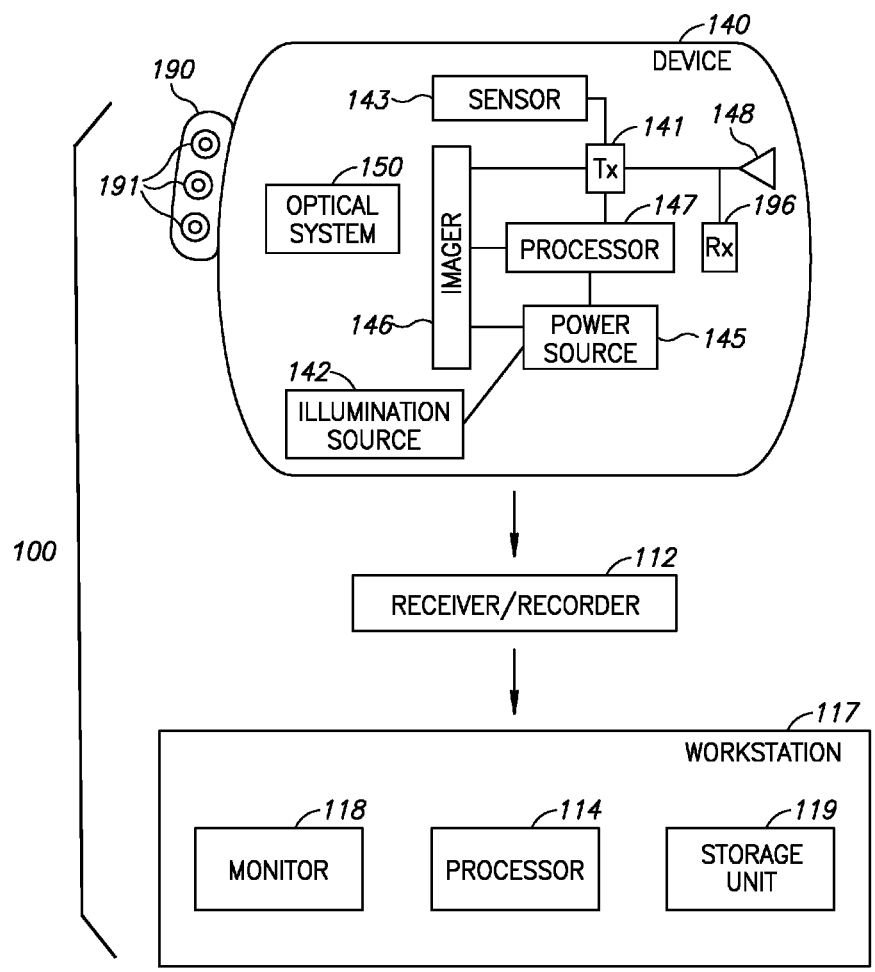
FIG. 1 is a schematic illustration of an in-vivo sensing system in accordance with some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Some embodiments of the present invention are directed to a typically one time use or partially single use detection and/or analysis device. Some embodiments are directed to a typically swallowable in-vivo device that may passively or actively progress through a body lime, e.g., the gastro-intestinal (GI) tract, for example, pushed along by natural peristalsis. Some embodiments are directed to in-vivo sensing devices that may be passed through other body lumens, for example, through blood vessels, the reproductive tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager. Other sensors may be included, for example, a pH sensor, a temperature sensor, a pressure sensor, sensors of other in-vivo parameters, sensors of various in-vivo substances or compounds, or the like. Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. patent application Ser. No. 09/800,470, entitled "A Device and System for In-Vivo Imaging", filed on Mar. 8, 2001, published on Nov. 1, 2001 as United States Patent Application Publication Number 2001/0035902, and/or in U.S. patent application Ser. No. 10/046,541, entitled "System and Method for Wide Field Imaging of Body Lumens", filed on Jan. 16, 2002, published on Aug. 15, 2002 as United States Patent Application Publication Number 2002/0109774, and/or in U.S. patent application Ser. No. 10/046,540, entitled "System and Method for Determining In-vivo Body Lumen Conditions", filed on Jan. 16, 2002, published on Aug. 15, 2002 as United States Patent Application Publication Number 2002/0111544, all of which are hereby incorporated by reference in their entirety. Devices and systems as described herein may have other configurations and/or sets of components. For example, an external receiver/recorder unit, a processor and a monitor, e.g., in a workstation, such as those described in the above publications, may be suitable for use with some embodiments of the present invention. Devices and systems as described herein may have other configurations and/or other sets of components. For example, the present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device. In other embodiments, an in-vivo device need not be swallowable and/or autonomous, and may have other shapes or configurations. Some embodiments may be used in various body lumens, for example, the GI tract, blood vessels, the urinary tract, the reproductive tract, or the like. In some embodiments, the in-vivo device may optionally include a sensor, an imager, and/or other suitable components.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

FIG. 1 is a schematic illustration of an in-vivo sensing system 100 in accordance with some embodiments of the invention. One or more components of system 100 may be used in conjunction with, or may be operatively associated with, the devices and/or components described herein or other in-vivo devices in accordance with embodiments of the invention. In some embodiments, system 100 may include a device 140 having a sensor, e.g., an imager 146, one or more illumination sources 142, a power source 145, and a transmitter 141. In some embodiments, device 140 may be implemented using a swallowable capsule, but other sorts of devices or suitable implementations may be used.

Device 140 typically may be or may include an autonomous swallowable capsule, but device 140 may have other shapes and need not be swallowable and/or autonomous. Embodiments of device 140 are typically autonomous, and are typically self-contained. For example, device 140 may be a capsule or other unit where all the components are substantially contained within a container or shell or housing, and where device 140 does not require any wires or cables to, for example, receive power and/or transmit information. In some embodiments, device 140 may be autonomous and non-remote-controllable; in another embodiment, device 140 may be partially or entirely remote-controllable.

Outside a patient's body may be, for example, an external receiver/recorder 112, which may include, or may associated with, one or more antennas (or antenna elements), optionally arranged as an antenna array. Receiver/recorder 112 may receive signals transmitted by the in-vivo device 140, for example, signals carrying image data, sensed data, control data, or the like. Receiver/recorder 112 may, for example, store the received data in a memory unit or a storage unit, or may display the information on a display unit (e.g., in real time or not in real time), for example, using hand-held device or computer.

Additionally, outside a patient's body may be, for example, a storage unit 119, a processor 114, and a monitor 118, which may optionally be implemented as a workstation 117, e.g., a computer or a computing platform. Workstation 117 may be connected to receiver/recorder 112 through a wireless or wired link or connection. Workstation 117 may receive from receiver/recorder 112 data that is received and/or recorded by receiver/recorder 112. In some embodiments, workstation 117 may receive the data from receiver/recorder 112 substantially in real-time, and/or while receiver/recorder 112 continues to receive and/or record data from the in-vivo device 140 and while the in-vivo device 140 is operational and/or in-vivo. In some embodiments, device 140 may communicate (e.g., directly or indirectly) with the external receiving and display system (e.g., workstation 117 or monitor 118) to provide display of data, control, or other functions.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, any other solid state camera or imager, a light detector, a linear imaging sensor, a line imaging sensor, a full frame imaging sensor, a "camera on chip" imaging sensor, a digital camera, a stills camera, a video camera, or other suitable imagers, cameras, or image acquisition components.

In some embodiments, transmitter 141 of device 140 may include a wireless transmitter, e.g., able to operate using radio waves, able to transmit Radio Frequency (RF) signals, or able to transmit other types of communication signals. For example, transmitter 141 may transmit wireless signals utilizing an antenna 148. In other embodiments, such as those where device 140 is or is included within an endoscope, transmitter 141 may transmit data via, for example, wire, cable, optical fiber and/or other suitable methods. Other known wired and/or wireless methods of transmission may be used.

In some embodiments, device 140 may optionally include a receiver 196, for example, a wired or wireless (e.g., RF) receiver, able to receive signals from an external transmitter. The received signals may include, for example, control signals or commands, e.g., to activate and/or otherwise control one or more components of device 140. Receiver 196 may receive signals, e.g., from outside the patient's body, for example, through antenna 148 or through a different antenna or receiving element. In some embodiments, signals or data may be received by a separate receiving unit in device 140. In some embodiments, transmitter 141 and receiver 196 may optionally be implemented using a transceiver unit or an integrated transmitter-receiver unit.

In some embodiments, imager 146 in device 140 may be operationally connected to transmitter 141. Transmitter 141 may transmit images and/or data to, for example, external transceiver or receiver/recorder 112 (e.g., through one or more antennas), which may send the data to processor 114 and/or to storage unit 119. Transmitter 141 may also include control capability, although control capability may be included in a separate component, e.g., a controller or processor 147. Transmitter 141 may include any suitable transmitter able to transmit image data, numerical data, other sensed data, and/or other data (e.g., control data) to a receiving device. Transmitter 141 may also be capable of receiving signals/commands, for example from an external transceiver. For example, in some embodiments, transmitter 141 may include an ultra low power Radio Frequency (RF) high bandwidth transmitter, possibly provided in Chip Scale Package (CSP).

In some embodiment, transmitter 141 may transmit/receive data via antenna 148. Transmitter 141 and/or another unit in device 140, e.g., a controller or processor 147, may include control capability, for example, one or more control modules, processing modules, circuitry and/or functionality for controlling device 140, for controlling the operational mode or settings of device 140, and/or for performing control operations or processing operations within device 140.

Power source 145 may include, for example, one or more batteries or power cells. For example, power source 145 may include silver oxide batteries, lithium batteries, other suitable electrochemical cells having a high energy density, or the like. Other suitable power sources may be used. For example, in some embodiments (e.g., where device 140 is, or is included in, an endoscope) power source 145 may receive power or energy from an external power source (e.g., an electromagnetic field generator), which may be external to device 140 and/or external to the body, and may be used to transmit power or energy to in-vivo device 140.

In some embodiments, power source 145 may be internal to device 140, and/or may not require coupling to an external power source, e.g., to receive power. Power source 145 may provide power to one or more components of device 140, for example, continuously, substantially continuously, or in a non-discrete manner or timing, or in a periodic manner, an intermittent manner, or an otherwise non-continuous manner. In some embodiments, power source 145 may provide power to one or more components of device 140, for example, not necessarily upon-demand, or not necessarily upon a triggering event or an external activation or external excitement.

Optionally, in some embodiments, transmitter 141 may include a processing unit or processor or controller (e.g., controller or processor 147), for example, to process signals and/or data generated by imager 146. In some embodiment, the processing unit may be an independent unit or integrated with another component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 141, and may be implemented, for example, using an ASIC.

In some embodiments, imager 146 may acquire in-vivo images, for example, continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 141 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 140 may include one or more illumination sources 142, for example one or more Light Emitting Diodes (LEDs), "white LEDs", monochromatic LEDs, Organic LEDs (O-LEDs), thin-film LEDs, single-color LED(s), multi-color LED(s), LED(s) emitting viewable light, LED(S) emitting non-viewable light, LED(s) emitting Infra Red (IR) light, an emissive electroluminescent layer or component, Organic Electro-Luminescence (OEL) layer or component, or other suitable light sources.

Illumination sources 142 may, for example, illuminate a body lumen or cavity being imaged and/or sensed. Device 140 may optionally include an optical system 150, for example, one or more optical elements, lenses, composite lens assemblies, magnifying lens, optical filters, prisms, gratings, plane mirrors, curved mirrors, concave mirrors or elements, convex mirrors or elements, reflective surfaces, reflective elements, light tunnels, light diverting elements, light focusing elements, or any other suitable optical elements. Optical system 150 may, for example, aid in focusing reflected light onto imager 146, focusing illuminated light, and/or performing other light processing operations.

In some embodiments, illumination source(s) 142 may illuminate continuously, or substantially continuously, for example, not necessarily upon-demand, or not necessarily upon a triggering event or an external activation or external excitement. In some embodiments, for example, illumination source(s) 142 may illuminate a pre-defined number of times per second (e.g., two or four times), substantially continuously, e.g., for a time period of two hours, four hours, eight hours, or the like; or in a periodic manner, an intermittent manner, or an otherwise non-continuous manner.

In some embodiments, the components of device 140 may be enclosed within a housing or shell, e.g., capsule-shaped, oblong, oval, spherical, tubular, peanut-shaped, or having other suitable shapes and/or dimensions. The housing or shell may be substantially transparent or semi-transparent, and/or may include one or more portions, windows or domes (e.g., a dome-shaped window, or multiple dome-shaped windows) which may be substantially transparent or semi-transparent. For example, one or more illumination source(s) 142 within device 140 may illuminate a body lumen through a transparent or semi-transparent portion, window or dome; and light reflected from the body lumen may enter the device 140, for example, through the same transparent or semi-transparent portion, window or dome (e.g., the window on dome on which liposomes or nanocontainers 191 may be located) or, optionally, through another transparent or semi-transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

Workstation 117 may include data processor 114 able to analyze the data received from device 140, and optionally able to separate images related to imaging the body lumen from images or data related to molecular analysis by the liposomes or nanoparticles 191. Data processor 114 may be in communication with storage unit 119, e.g., able to transfer frame data to and/or from storage unit 119. Data processor 114 may provide the analyzed data to monitor 118, where a user (e.g., a physician) may view or otherwise use the presented data. Data processor 114 may analyze the data received via external receiver/recorder 112 or (e.g., directly) from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 and/or workstation 117 may be configured for real time processing, and/or may be implemented using a hand-held device. In another embodiment, post processing may be performed, and data or images may be viewed at a later time (e.g., not in real time). In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. According to other embodiments a 320×320 pixel imager may be used. Pixel size may be, for example, between 5 to 6 microns; other suitable sizes may be used. According to some embodiments, pixels may be each fitted with a micro lens. For example, a Bayer color filter may be applied. Other suitable data formats may be used, and other suitable numbers or types of rows, columns, arrays, pixels, sub-pixels, boxes, super-pixels and/or colors may be used.

Optionally, device 140 may include one or more sensors 143, instead of or in addition to a sensor such as imager 146. Sensor 143 may, for example, sense, detect, determine and/or measure one or more values of properties or characteristics of the surrounding of device 140. For example, sensor 143 may include a pH sensor, a temperature sensor, an electrical conductivity sensor, a pressure sensor, or any other known suitable in-vivo sensor.

In some embodiments, device 140 may include a carrier substance 190, e.g., a hydrogel, which may be immobilized or otherwise mounted or coated on an external portion of device 140, e.g., over a dome-shaped optical window of device 140. Carrier substance 190 may include, for example, conjugated liposomes or nano-containers 191.

In some embodiments, carrier substance 190 may be made of or may include crosslinked polymeric chains, in which water or water-based solutions may be dispersed or adsorbed, for example, a hydrogel, e.g., a network of polymer chains that are water-soluble, or a colloidal gel in which water is the dispersion medium, or micelles or polymeric compounds, e.g., cellulose; other absorbent or super-absorbent natural or synthetic polymers may be used. In another embodiment, dried formulations may be used, e.g. lyophilize liposomes or polymersomes may be embedded in nitrocellulose. In other embodiments, preservatives (e.g., Thimerosal, benzyl alcohol, parabens, or the like) may be used or added.

Figure 2:
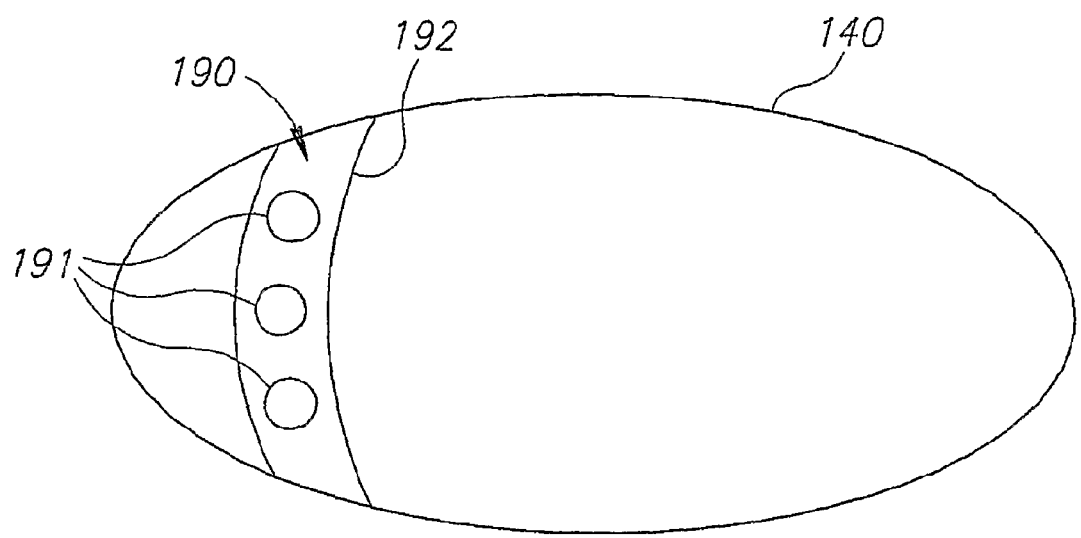
FIG. 2 is a schematic illustration of an in-vivo imaging device in accordance with an embodiment of the invention.

In some embodiments, for example, as illustrated in FIG. 2, carrier substance 190 and liposomes or nano-containers 191 may be placed in, or immobilized onto, a band 192, e.g., mounted or coated around or over a portion of device 140, or around or over a portion of a window or a suitable trench in the dome-shaped window of device 140.

Figure 3:
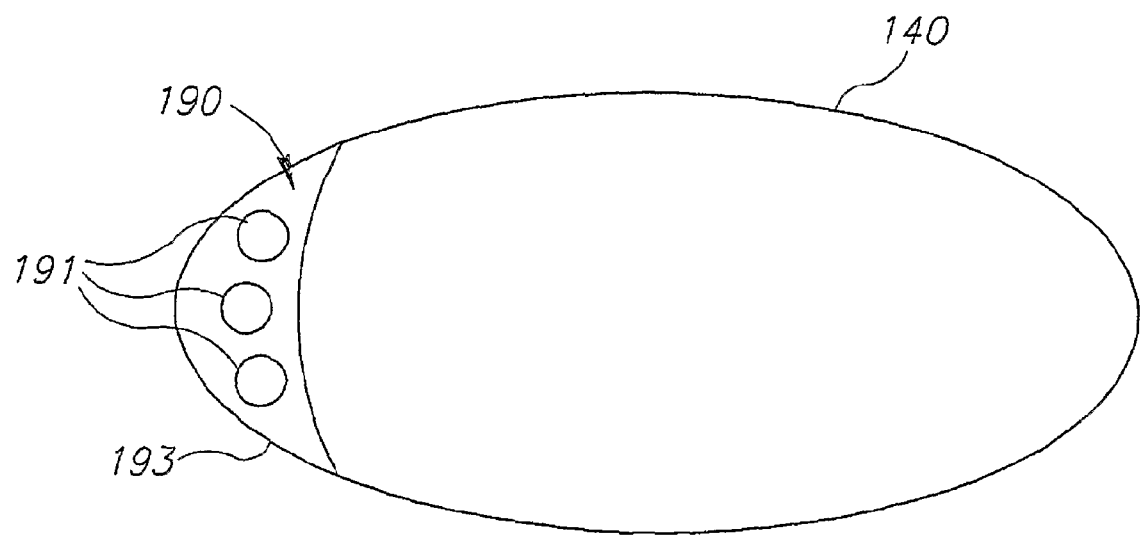
FIG. 3 is a schematic illustration of an in-vivo imaging device in accordance with another embodiment of the invention.

In some embodiments, for example, as illustrated in FIG. 3, carrier substance 190 and liposomes or nano-containers 191 may be placed in, or immobilized onto, an external dome-shaped portion 193, e.g., mounted or coated over a portion of device 140, or around or over a window or dome-shaped window of device 140.

In some embodiments, the carrier substance 190 (e.g., hydrogel) may be coated, for example, for preservation and/or storage while the device 140 is not in-vivo. For example, the coating may dissolve in-vivo, or only when the device 140 reaches a certain body part (e.g., the colon). In some embodiments, the coating may partially dissolve, for example, to open an inlet gate and/or an outlet gate, thereby creating a flow (e.g., a contuse flow) through the carrier substance 190.

Although FIG. 2 and FIG. 3 demonstrate the placement of carrier substance 190 and liposomes or nano-containers 191 externally to the in-vivo device 140, other suitable locations may be used. In some embodiments, for example, carrier substance 190 and liposomes or nano-containers 191 may be placed internally to device 140, e.g., within an internal compartment or chamber or channel, which may be subsequently opened in-vivo (e.g., using a dissolvable gate, a mechanical gate, or the like). Other suitable placement, mounting or coating methods may be used.

For example, in some embodiments, a reaction chamber within the in-vivo device 140 or connected to the in-vivo device 140 may contain immobilized the liposomes or nano-containers 191 for carrying imaging agents that may be specifically reactant to a target analyte. Such liposomes or nano-containers 191 may include, for example, liposomes, colloidosomes and/or polymerosomes; other suitable nano-containers may be used. In some embodiments, for example, liposomes or nano-containers 191 may include bilayers of phospholipids around a hydrophobic core; in other embodiments, liposomes or nano-containers 191 may be composed of more than bilayers and may include a multilayer of confronting lipid layers.

In some embodiments, conjugated liposomes or nano-containers 191 (e.g., lyophilezed conjugated liposomes, or a liposome having a conjugated antibody integrated therein) may be filled with, for example, pH sensitive color in low strength buffer possessing a pH different from and/or opposite that of the sample and/or analyte. Rupture of the liposomes or nano-containers 191 may occur as a result of a reaction with a target analyte. Upon rupturing of the liposomes or nano-containers 191 and exposure of, for example, the pH sensitive color to the sample, a change of color may occur that may be, for example, optically detectable and/or visible and/or may be imaged. In other embodiments, liposomes or nano-containers 191, e.g., polymersome, may include or may be filled with an alternate or additional molecule (e.g., fluorescence material, material having fluorescence properties, or the like) capable of changing optical properties of a substrate.

Figure 4A:
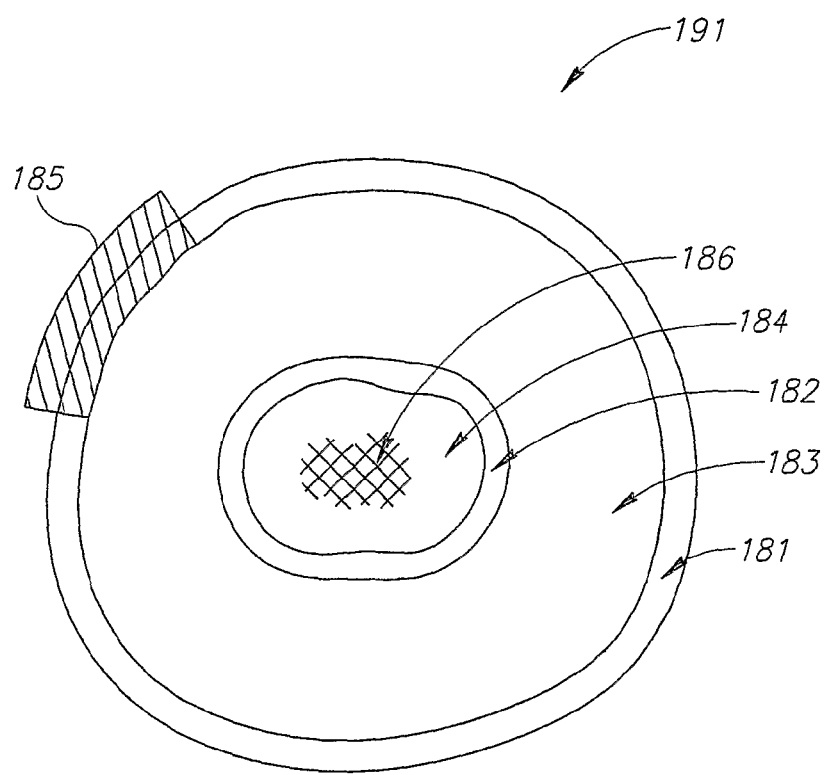
FIG. 4A is a schematic illustration of a liposome or nano-container in accordance with some embodiments of the invention.
Figure 4B:
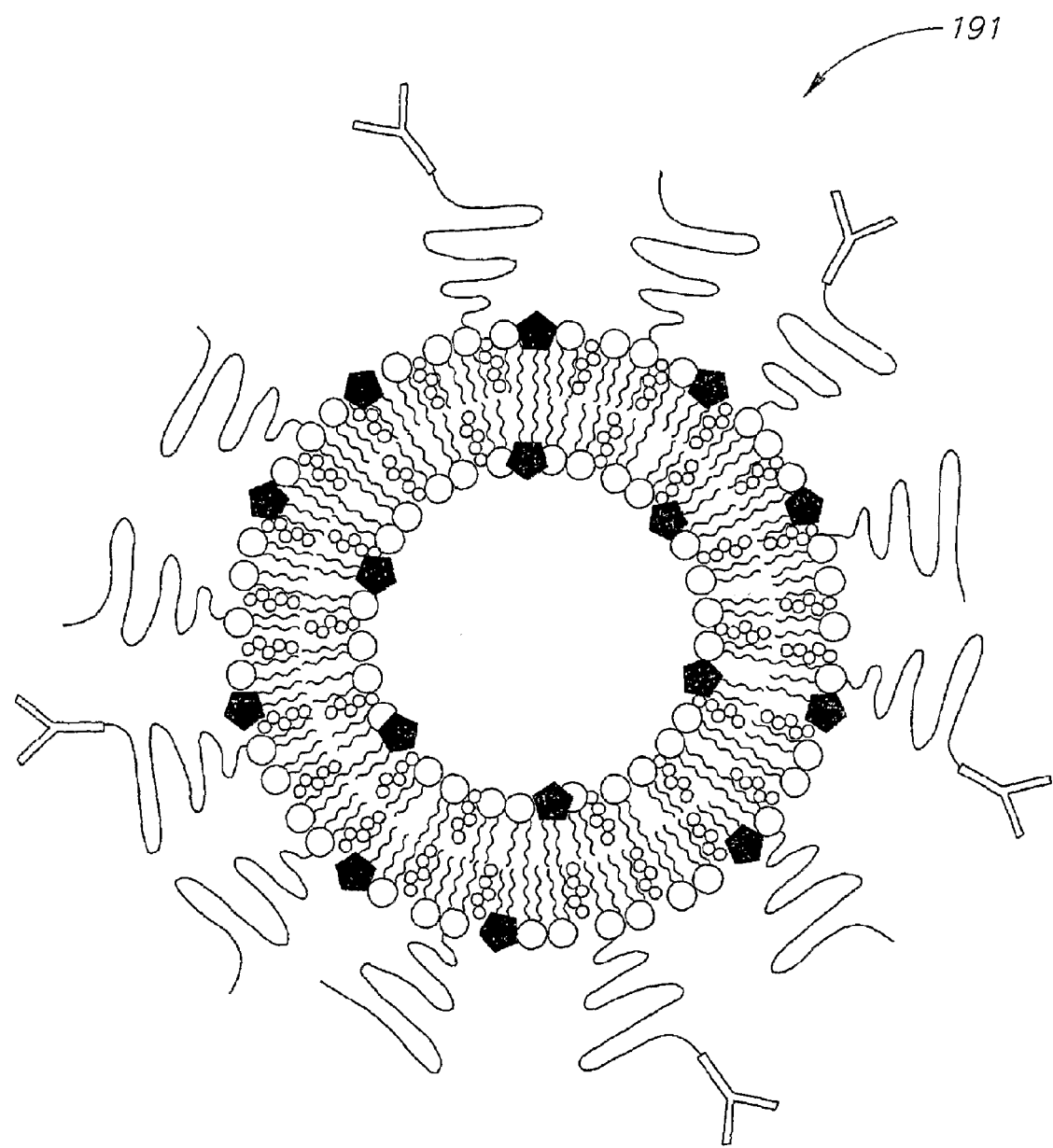
FIG. 4B is an illustration of a liposome or nano-container in accordance with some embodiments of the invention.

Reference is made to FIG. 4A, which illustrates a liposome or nano-container 191 in accordance with some embodiments of the invention, and to FIG. 4B, which illustrates a liposome or nano-container 191 in accordance with, some embodiments of the invention. Liposome or nano-container 191 may be or may include, for example, a microscopic self-assembling spherical vesicle (e.g., liposome, nanosome, or the like) having a membrane composed of, e.g., a phospholipid bilayer. Liposome or nano-container 191 may include, for example, organic materials, inorganic materials, synthetic materials or polymers, polyphosphate-based materials, or the like. Liposome or nano-container 191 may be a fluid-filled pouch or compartment, whose walls are made of layers of phospholipids which may be substantially identical to the phospholipids of cell membranes. Liposome or nano-container 191 may have a diameter of approximately 50 nanometers, approximately 100 nanometers, or the like.

In some embodiments, for example, a first shell 181, e.g., an external shell, of the liposome or nano-container 191 may be water insoluble; whereas a second shell 182, e.g., an internal shell, of the liposome or nano-container 191 may be water soluble. In some embodiments, for example, a zone between the first shell 181 and the second shell may be used as a first nano-compartment 183, e.g., a hydrophobic cavity; whereas a zone inside the second shell 182 may be used as a second nano-compartment 184, e.g., a polar cavity. Other numbers or locations of layers, shells, zones and/or nano-compartments may be used.

In some embodiments, an external layer (or a portion of an external layer) of the liposome or nano-container 191 may include, or may be connected to, a reactant or reagent 185. For example, the reactant or reagent 185 may be or may include a protein, a hormone, an enzyme, an antibody, a targeting agent, an active part of an antibody, a "hotspot" of an antibody or a protein (e.g., minimal functional domains involved in protein-to-protein interactions and sufficient to induce a biological or chemical response), a modified antibody, a modified antigen, or the like. For example, reactant or reagent 185 may include a specific protein or antibody which may react when in contact with a certain antigen or pathology, e.g., a tumor, a cancerous tumor, an infection, a polyp, or the like. In some embodiments, for example, reactant or reagent 185 may include, for example, pepsin, pepsin 1, pepsin 3, gastrin, gastrin 17, or various other reactants or reagents.

In some embodiments, liposome or nano-container 191 may store therein (e.g., within nano-compartment 183 and/or 184) a signaling material 186. The signaling material 186 may be or may include, for example, a pH-sensitive substance or indicator, a fluorescent substance or indicator, or another substance or indicator which may modify its optical properties (e.g., its color or its light emission or absorption properties) upon modification of the signaling material 186 or upon reaction between the signaling material 186 and another substance (e.g., targeted protein or an analyte present in body fluid). For example, in some embodiments, signaling material 186 may initially (e.g., when stored within liposome or nano-container 191) have a first color, e.g., blue; and may modify its color to a second, different color, e.g., yellow, if signaling material 186 reacts with a body substance or with another material substance present in hydrogel 190.

In some embodiments, for example, signaling material 186 may have a first color or a first fluorescence or a first optical property in the presence of a first substance, and a second color or a second fluorescence or a second optical property in the presence of a second substance. In some embodiments, for example, signaling material 186 may have a first color or a first fluorescence or a first optical property in the presence of a first pH level or a first acidity level, and a second color or a second fluorescence or a second optical property in the presence of a second pH level or a second acidity level. In some embodiments, for example, signaling material 186 may have a first color or a first fluorescence or a first optical property in the presence of a water-based substance, and a second color or a second fluorescence or a second optical property in the presence of a lipid-based substance.

Referring again to FIG. 1, the device 140 may be inserted in-vivo, for example, by swallowing a swallowable capsule, and may pass through a body lumen. The liposome or nano-container 191 may be in contact with a body substance which may react with reactant or reagent 185, e.g., a certain antigen or pathology, a tumor, a cancerous tumor, an infection, a polyp, or the like. The reaction may cause breaking, opening, rupture, collapsing, dissolution, fusion, or puncturing of liposome or nano-container 191, or of one or more layers (e.g., an external layer, or a portion thereof) of liposome or nano-container 191. For example, one or more holes, outlets, punctures or openings may be created, allowing the signaling material 186 stored within liposome or nano-container 191 to exit and/or to be in contact with the body substance or with the carrier substance 190 (e.g., the hydrogel); thereby resulting in a modification of an optical property of signaling material 186 (e.g., color or fluorescence; for example, modification from blue color to yellow color, or the like).

In some embodiments, for example, signaling material 186 may include or may be bromothymol blue (indicator) in a solution with low buffer capacity at a pH of approximately 8 or above having a blue color. When liposome or nano-container 191 is in contact with healthy stomach acid, the acid may not penetrate the liposome or nano-container 191, there may be no contact between the acid and the signaling material 186 (e.g., the indicator), and thus liposome or nano-container 191 may remain blue. In contrast, if the stomach acid contains targeted proteins, e.g., above a threshold value, liposome or nano-container 191 may deteriorate, the stomach acid may be in contact with the signaling material 186 (e.g., the indicator), and the signaling material 186 (e.g., the indicator) may modify its color (or other optical property), e.g., from blue to yellow.

In some embodiments, the modification of optical property of the signaling material 186, or the resulting optical property of signaling material 186, may be imaged or otherwise sensed, e.g., by imager 146 of in-vivo device 140. For example, imager 146 may acquire one or more images, e.g., through a window or a dome-shaped window of device 140. The acquired image may include, for example, the signaling material 186 having a modified (e.g., non-original) color, and/or a body lumen in which the reaction takes place. The detection of the modification of the optical property of signaling material 186, and/or the detection of signaling material 186 which may now be external to the liposome or nano-container 191, may indicate that a reactance took place between reagent or reactant 185 and its corresponding antigen, and may indicate the presence of the corresponding antigen, e.g., a pathology, a tumor, a cancerous tumor, an infection, a polyp, or the like.

In some embodiments, for example, the liposome or nano-container 191 may be initially filled with pH-sensitive substance having a first color (e.g., blue). The liposome or nano-container 191 may rupture as a result of reaction with a target, e.g., a certain antigen. The pH-sensitive substance stored within the liposome or nano-container 191 may modify its color into a second color (e.g., yellow). The in-vivo imager 146 may acquire images of the modified color, and the image data may be transmitted by transmitter 141.

In some embodiments, device 140 may transmit digital color image information which may include color information of the liposome or nano-container 191, e.g., in discrete portions; for example, a discrete portion may correspond to an image or a frame; other suitable transmission methods may be used. In some embodiments, device 140 may capture and/or acquire an image, for example, once every half second; other capture rates, constant or variable, may be used. In some embodiments, device 140 may be used for locating the disorder or pathology, and/or for determining its nature, e.g., distinguishing between a benign and malignant polyps or tumors.

In other embodiments, for example, the liposome or nano-container 191 may be initially filled with fluorescent substance. The liposome or nano-container 191 may rupture as a result of reaction with a target, e.g., a certain antigen. The fluorescent substance stored within the liposome or nano-container 191 may be exposed or may exit the liposome or nano-container 191 and as a result change (e.g., increase) its excitation properties. The in-vivo imager 146 or the sensor 143 (e.g., a light sensor) may acquire the images and/or the change (e.g., increase) in signal of the fluorescent substance, and the sensed data may be transmitted by transmitter 141, e.g., in addition to or instead of the relevant image data.

In some embodiments, in-vivo device 140 may be localized, e.g., using one or more localization methods, thereby allowing to determine the location or body part in which the reaction took place, e.g., the location or body part having the antigen, pathology, tumor, cancerous tumor, infection, polyp, or the like.

Figure 5:
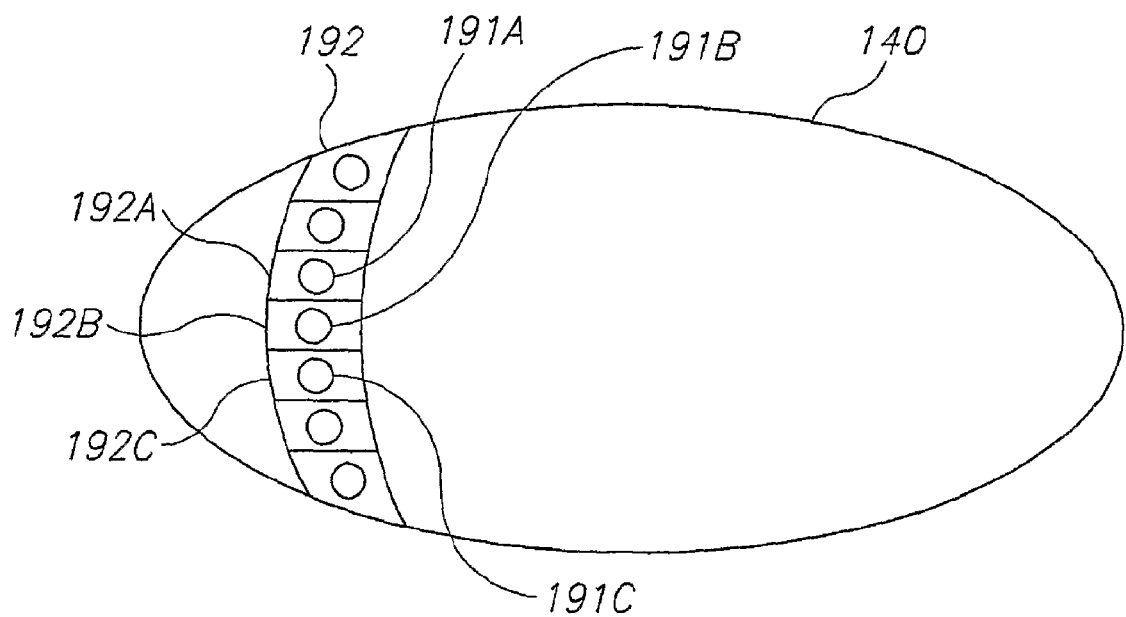
FIG. 5 is a schematic illustration of an in-vivo imaging device in accordance with yet another embodiment of the invention.

FIG. 5 illustrates an in-vivo device 140 having multiple types of liposomes or nano-containers 191, in accordance with some embodiments of the invention. For example, carrier substance 190 and liposomes or nano-containers 191 may be placed in, or immobilized onto, a band 192, e.g., mounted or coated around or over a portion of device 140, or around or over a portion of a window or dome-shaped window of device 140. Band 192 may include multiple portions or areas, for example, a first portion 192A, a second portion 192B, a third portion 192C, or the like; and each portion may include, for example, a different type of liposomes or nano-containers, e.g., a first type of liposomes or nano-containers 191A, a second type of liposomes or nano-containers 191B, a third type of liposomes or nano-containers 191C, respectively. For example, the first type of liposomes or nano-containers 191A may be adapted to react to a first antigen or protein, the second type of liposomes or nano-containers 191A may be adapted to react to an enzyme or protein, the third type of liposomes or nano-containers 191A may be adapted to react to a tertian hormone or protein, or the like.

In-vivo device 140 of FIG. 5 may pass through a body lumen, e.g., the GI tract. The first type of liposomes or nano-containers 191A may be in contact with the first antigen or protein, thereby causing rupture of the liposome or nano-container 191A, and modification of optical property of the content of liposome or nano-containers 191A. Similarly, third type of liposomes or nano-containers 191C may be in contact with the hormone or third protein, thereby causing rupture of the liposome or nano-container 191C, and modification of optical property of the content of liposome or nano-container 191C. In contrast, the second type of liposomes or nano-containers 191B may not be in contact with the enzyme or second protein (e.g., if the enzyme is not present in the patient's body or GI tract), and the content of the second type of liposome or nano-container 191B may not be exposed or may not modify its optical property. Device 140 may acquire images including the first portion 192A, the second portion 192B, and the third portion 192C. The in-vivo images may indicate, for example, that the first and third antigens are detected and may be present in-vivo, whereas the second antigen are not detected and possible may not be present in-vivo.

In some embodiments, reaction by the first type of liposomes or nano-containers 191A may result in a first modification of optical property (e.g., change of color from blue to yellow), whereas reaction by the by the second type of liposomes or nano-containers 191B may result in a second, different, modification of optical property (e.g., change of color from blue to green, or exposure of fluorescent substance).

In some embodiments, reaction by a first type of liposomes or nano-containers 191A may result in a first modification of optical property (e.g., change of color from blue to yellow); whereas reaction by the by a second type of liposomes or nano-containers 191B may result in a second, different, modification of non-optical properties, e.g., modification in magnetic field or conductivity, which may be detected by sensor 143.

In other embodiments, multiple reactions may result in similar, or even substantially identical, modifications of optical property, and may be differentiated or distinguished, for example, based on the location or the relative location of the portions. For example, a change of color from blue to yellow in the first portion 192A, may be distinguished from a change of color from blue to yellow in the third portion 192C, based on the location or the relative location of portions 192A and 192C on the band 192 as imaged by the in-vivo device 140. For example, a change of color from a first color to a second color at the location of the first portion 192A, may be used as indication that the first type of liposomes or nano-containers 191A reacted with a first type of antigen; whereas a change of color from the first color to the second color at the location of the first portion 192C, may be used as indication that the third type of liposomes or nano-containers 191C reacted with a third type of antigen.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An in-vivo imaging device comprising:
a housing, said housing comprising a window coated with a first and second type of rupturable liposomes, each of said rupturable liposomes containing a signaling marker, wherein the first type of rupturable liposomes rupture in the presence of a first target analyte and the second type of rupturable liposomes rupture in the presence of a second target analyte, thereby releasing said signaling markers from said first and second types of rupturable liposomes and resulting in a modification of an optical property of said signaling markers;
an illumination source located within the housing to illuminate a body lumen through the window;
an imager to receive light reflected from the body lumen through the window; and
a transmitter to transmit image data to a receiving system.

2. The imaging device according to claim 1, wherein the housing is capsule shaped.

3. The imaging device according to claim 1, wherein the imager acquires images including the modified optical property of said signaling marker.

4. The imaging device according to claim 1, wherein the rupturable liposomes are coated on an external portion of the window.

5. The imaging device according to claim 1, wherein the rupturable liposomes are immobilized in a carrier substance.

6. The imaging device according to claim 5, wherein the carrier substance is arranged as a band around a portion of the imaging device.

7. The imaging device according to claim 6, wherein the band further comprises a first area and at least a second area, wherein each area comprises a type of rupturable liposomes.

8. The imaging device according to claim 6, wherein the band further comprises a first area comprising said first type of rupturable liposomes and a second area comprising said second type of rupturable liposomes.

* * * * *